(12) United States Patent
Pologe et al.

(10) Patent No.: US 7,430,444 B2
(45) Date of Patent: Sep. 30, 2008

(54) PHOTOPLETHYSMOGRAPHIC DEVICE WITH SPECIES-SPECIFIC CALIBRATION

(75) Inventors: Jonas Alexander Pologe, Boulder, CO (US); Kurt Albert Aronow, Louisville, CO (US)

(73) Assignee: Kestrel Lab, Inc., Boulder, CO (US)

( * ) Notice: Subject to any disclaimer, the term of this patent is extended or adjusted under 35 U.S.C. 154(b) by 0 days.

(21) Appl. No.: 11/412,013

(22) Filed: Apr. 27, 2006

(65) Prior Publication Data

US 2007/0255124 A1   Nov. 1, 2007

(51) Int. Cl.
*A61B 5/1455* (2006.01)
(52) U.S. Cl. .................................. 600/322; 600/310
(58) Field of Classification Search ................ 600/300, 600/309, 310, 322, 323, 331
See application file for complete search history.

(56) References Cited

U.S. PATENT DOCUMENTS

| | | | | |
|---|---|---|---|---|
| 5,058,587 A | * | 10/1991 | Kohno et al. | 600/328 |
| 5,800,349 A | * | 9/1998 | Isaacson et al. | 600/323 |
| 5,931,779 A | * | 8/1999 | Arakaki et al. | 600/310 |
| 6,421,549 B1 | * | 7/2002 | Jacques | 600/331 |
| 2002/0010390 A1 | * | 1/2002 | Guice et al. | 600/300 |
| 2004/0024297 A1 | * | 2/2004 | Chen et al. | 600/323 |
| 2004/0073100 A1 | * | 4/2004 | Ballerstadt et al. | 600/316 |
| 2004/0138539 A1 | * | 7/2004 | Jay et al. | 600/322 |
| 2004/0204639 A1 | * | 10/2004 | Casciani et al. | 600/338 |

\* cited by examiner

*Primary Examiner*—Eric F Winakur
*Assistant Examiner*—Etsub D Berhanu

(57) ABSTRACT

A method and apparatus for photoplethysmographic measurements from non-human species is disclosed. The extinction of light by hemoglobin, as a function of wavelength, varies as a function of the species of the subject being monitored. The calibration of a photoplethysmographic device should therefore also vary dependant upon the species of the subject. The photoplethysmographic device of this invention includes calibrations specifically designed to provide accurate readings on non-human subjects.

4 Claims, 4 Drawing Sheets

PHOTOPLETHYSMOGRAPHIC DEVICE WITH SPECIES-SPECIFIC CALIBRATION

BACKGROUND OF THE INVENTION

This invention is in the field of noninvasive medical monitoring and more specifically in photoplethysmographic monitoring and provides improved measurement accuracy when performing photoplethysmographic measurements on one or more animal species.

In the science of photoplethysmography, light is used to illuminate or trans-illuminate living tissue for the purpose of providing noninvasive measurements of blood analytes or other hemodynamic parameters or tissue properties. In this monitoring modality light is directed into living tissue and a portion of the light which is not absorbed by the tissues, or scattered off in some other direction, is detected a short distance from the entry point. The detected light is converted into an electronic signal that is indicative of the received light signal from the tissue. These signals, one for each emitter, or spectral band of light incident on the tissue-under-test, vary with the pulsation of the blood through the tissue-under-test and are referred to as photoplethysmographic signals. These photoplethysmographic signals are then used to calculate blood analytes such as arterial blood oxygen saturation and hemodynamic variables such as heart rate, cardiac output, or tissue perfusion. Among the blood analytes that may be measured by photoplethysmography are the various types of hemoglobin, including the percentages of oxyhemoglobin, carboxyhemoglobin, methemoglobin, and reduced hemoglobin in the arterial blood. A device which detects and processes photoplethysmographic signals to measure the levels of various blood analytes and various hemodynamic parameters is referred to as a photoplethysmographic measurement apparatus, device, or instrument.

The first widespread commercial use of a photoplethysmographic measurement apparatus in medicine was in the pulse oximeter, a device designed to measure arterial blood oxygen saturation. To make these measurements at least two different bands of light must be used with each light band possessing a unique spectral content. Each spectral band, or light band, is typically referred to by the center wavelength, or sometimes by the peak wavelength, of the given band. In conventional pulse oximetry two different emitters such as light emitting diodes (LEDs) are commonly used to generate the sensing light. Usually one LED has a center, or peak, wavelength near 660 nanometers (nm) and a second has a center, or peak, wavelength near 900 nm. More recently photoplethysmographic instruments have been developed in which more than two light bands are utilized to allow the measurement of a larger number of blood analytes including carboxyhemoglobin, methemoglobin, and reduced hemoglobin.

Light from each emitter (each light band) is incident on the tissue-under-test, which, for people, usually consists of a finger, earlobe, or other relatively thin tissue site which is well perfused with blood. On non-human species, such as dogs, cats, or other animal species, the tissue-under-test may be the pinna of the ear, the buccal mucosa, the tongue, the web of the toes, or some other acceptable site for transmission or reflectance measurement of photoplethysmographic signals. After passing some distance through the tissue-under-test, a portion of the light not absorbed by the tissue or scattered in some other direction is collected by a detector such as a photodiode and converted into electronic signals that are proportional to the received light signals. The channels, or electronic signals from each of the different light sources, are kept separated or can be separated later through the use of any one of a number of different well-published techniques, including but not limited to, time-division multiplexing or frequency-division multiplexing.

These photoplethysmographic signals received from the tissue consist of a small pulsatile component and a rather large relatively constant component that changes slowly over time when compared with the pulsatile component of the signal. The pulsatile component of the photoplethysmographic signal is created by the pulsation of the blood in the tissue-under-test. When the heart contracts, blood is pushed out of the heart and into the peripheral tissues. This increases the optical density of the tissue located between the emitter and detector elements of the sensor, which decreases the amplitude of the received optical signals. As the heart relaxes and refills with blood the optical density of the tissue-under-test decreases and the received signal amplitude increases. The comparatively constant component of the photoplethysmographic signal is often referred to as the DC component of the signal, and the pulsatile component of the photoplethysmographic signal is often referred to as the AC component of the signal.

The photoplethysmographic signals, after being converted into electronic signals, are processed through the signal processing circuitry to obtain a measurement of the desired blood analytes and, or, hemodynamic parameters which in the case of pulse oximetry typically consists of oxygen saturation in the arterial blood and the heart rate. The signal processing circuitry varies from manufacturer to manufacturer but typically incorporates the steps of amplifying the signals, filtering out unwanted frequencies, and converting the signals into the digital domain. Once in digital form the signals are run through a calibration to determine the desired blood analyte levels. The calibration is any method, means, algorithm, software, equations, or even analog circuitry, which associate the photoplethysmographic signals, with the desired blood analyte level. The steps defined in this paragraph can be carried out by analog circuitry or the photoplethysmographic signals can be converted into the digital domain almost immediately after the photo-detection and these same steps can be performed by manipulation of the digital signals.

In conventional pulse oximetry the calibration is typically an equation (or one of a series of equations selected based on the spectral content of the specific emitters used) which convert the photoplethysmographic signals obtained from the tissue-under-test, after the electronic signal processing, into the measurement of arterial oxygen saturation.

These calibrations or calibration equations are usually derived empirically by performing "desaturation" studies on healthy human volunteers where the photoplethysmographic signals are correlated with invasive measurements of arterial oxygen saturation, or other desired blood analytes of interest. While this work has generated numerous accurate commercial pulse oximeters for use on human subjects, the need to provide species-specific calibrations for photoplethysmographic devices designed for the measurement of blood analytes and or hemodynamic parameters on non-human subjects has remained unmet.

The need for accurate noninvasive measurement of arterial oxygen saturation in veterinary medicine is in some ways even greater than it is for human use. This stems from the fact that there are so few monitoring modalities designed and built specifically for use in veterinary medicine. This can make it extremely difficult to adequately monitor animals during veterinary procedures, thus increasing the morbidity and mortality associated with such procedures.

While some medical monitors designed for use on humans, such as ECG for example, perform accurately on non-human species, this is not the case for photoplethysmographic measurements. Photoplethysmographic measurements of various types of hemoglobin, such as oxyhemoglobin, carboxyhemoglobin, methemoglobin, and reduced hemoglobin, are dependant on the extinction curves of these various types of hemoglobin. Extinction curves define the absorption of light by a given material as a function of wavelength. The reason one calibration (or one set of calibrations designed to account of the different spectral contents of different emitters) works accurately for all human patients is because the extinction curves of human adult hemoglobin is the same from one person to the next. This is not true across species.

W G Zijlstra et al in 2000 published a book entitled *Visible and Near Infrared Absorption Spectra of Human and Animal Haemoglobin, Determination and Application*, in which they provided the measurements of the extinctions of the four primary types of hemoglobin for several different species including, human, dog, rat, bovine, pig, horse, and sheep. Analysis of these extinction curves show differences between the species that result in significant measurement errors when a human calibrated pulse oximeter is used on a non-human subject. These errors vary by species and by oxygen saturation level.

This species-to-species variability in pulse oximetry measurements has been demonstrated by N. S. Matthews, et al in their 2003 paper entitled An Evaluation of Pulse Oximeters in Dogs, Cats, and Horses, where they observed that "monitors appeared to perform differently on different species while the techniques and sampling methods were similar."

Nonetheless all pulse oximeters in veterinary use today contain only one calibration (or set of calibrations for the purpose of accounting for the different spectral contents of specific emitters used in the different sensors) which is used regardless of the species of the patient. These photoplethysmographic instruments contain human calibrations which are typically inaccurate when used on non-human subjects and do not in any way compensate for the differences in optical properties from one species to the next.

BRIEF SUMMARY OF THE INVENTION

The object of this invention is to provide a monitor with user selectable, species-specific calibrations, to assure accurate photoplethysmographic measurements of blood analytes or hemodynamic parameters on a wide range of different animal species.

Extinction curves for hemoglobin vary by species, which imposes measurement error on photoplethysmographic measurements performed on animal species using photoplethysmographic devices calibrated for use on humans. In this invention a photoplethysmographic device is specifically calibrated for use on one or more animal (non-human) species. Calibration is the association between the photoplethysmographic signals received by the sensor and the blood analyte level displayed by the instrument. In this invention the calibration or calibrations are designed to accurately convert the photoplethysmographic signals measured on one or more animal species into the desired blood analyte such as arterial oxygen saturation ($O_2Hb$), arterial reduced hemoglobin level (RHb), carboxyhemoglobin level (COHb), or methemoglobin level (metHb).

Three key elements must be provided to create an instrument capable of accurate measurement on multiple animal species: the calibrations must be derived for each desired species; the instrument must be programmed with, or otherwise designed to include, each of the desired calibrations; and the instrument must include a means for selecting the "active calibration". The "active calibration" is the calibration that is being used by the instrument at any given time to convert the photoplethysmographic data into the desired blood analyte levels.

To derive the calibration for any given species, a number of different methodologies can be employed. In pulse oximetry on humans, the calibrations are almost always developed by performing numerous tests on several human subjects that pair photoplethysmographic signals, or some mathematical representation thereof, with the arterial oxygen saturation of the test subject, over a wide range of oxygen saturation levels. This "desaturation study" data provides the information necessary to create the calibration.

The sensors used on any given photoplethysmographic instrument may contain emitters whose spectral contents are not exactly the same from one sensor to the next. It may therefore be necessary to develop several different calibrations to account for these variations. This is a well known consideration in the design and manufacture of pulse oximeters and has long been solved by providing a group of calibrations (or calibration curves) that vary from one to the next to assure that the calibration used in association with any given sensor, and its specific emitter set, accurately associates the measured photoplethysmographic data with the correct oxygen saturation value to be displayed. While this group of calibrations can accurately compensate for the effects of differences in the spectral content of different emitters, it does nothing to correct for errors caused by the differences in the optical extinction of the hemoglobin caused by variations in the molecular composition of the hemoglobin molecule itself from one species to the next.

In this patent a single calibration, that associates one specific species photoplethysmographic data to one or more blood analyte levels, or a group of different calibrations that perform the same purpose and which also compensates for the variability in the spectral content of different emitters, is considered to be a single calibration. In this invention, a set of calibrations is created, each one unique to a given species and to the blood analyte or blood analytes of interest. Such an instrument properly accounts for the variations in the extinction curves of blood analytes from one species to another. While this discussion specifically refers to the measurement of the various types of hemoglobin, other blood analytes may also require species-specific calibrations.

In the preferred embodiment of this invention a single photoplethysmographic instrument will have a set of calibrations installed in it, each one corresponding to a different species. Typically these calibrations would be installed in the software of the instrument. The calibration appropriate for the species being monitored could be selected in any one of a number of different ways. In the current embodiment the user of the instrument manually selects the calibration to be used, i.e. the active calibration, through the user interface.

An alternate method for selection of the active calibration would be more automated. The instrument's sensors could be designed to be used only for a single species, or group of species, with acceptably similar extinction curves for the analyte or analytes of interest. These sensors would contain an identification element that, when connected to the instrument would be interrogated by the instrument to allow it to select the correct calibration for the attached sensor and the specific species on which it was calibrated.

DETAILED DESCRIPTION OF THE INVENTION

In conventional pulse oximetry the calibration is typically developed by running a desaturation study. In these studies photoplethysmographic data are collected at a number of different oxygen saturation levels and these data are paired with simultaneously measured arterial oxygen saturation ($O_2Hb$) measurements. The $O_2Hb$ measurements are made by running arterial blood samples through a laboratory analyzer. The photoplethysmographic data, for two wavelength pulse oximetry, are often converted into a ratio, R, which is indicative of the received photoplethysmographic signals. R is usually a ratio indicative of the absorption (or differential absorption) of the arterial blood at one wavelength, typically abut 660 nm, ($A_{660nm}$) divided by the absorption (or differential absorption) of the arterial blood at a second wavelength, typically about 900 nm ($A_{900nm}$). In this example R would be defined by Equation 1.

$$R = A_{660nm}/A_{900nm} \quad \text{Equation 1}$$

Figure 1:
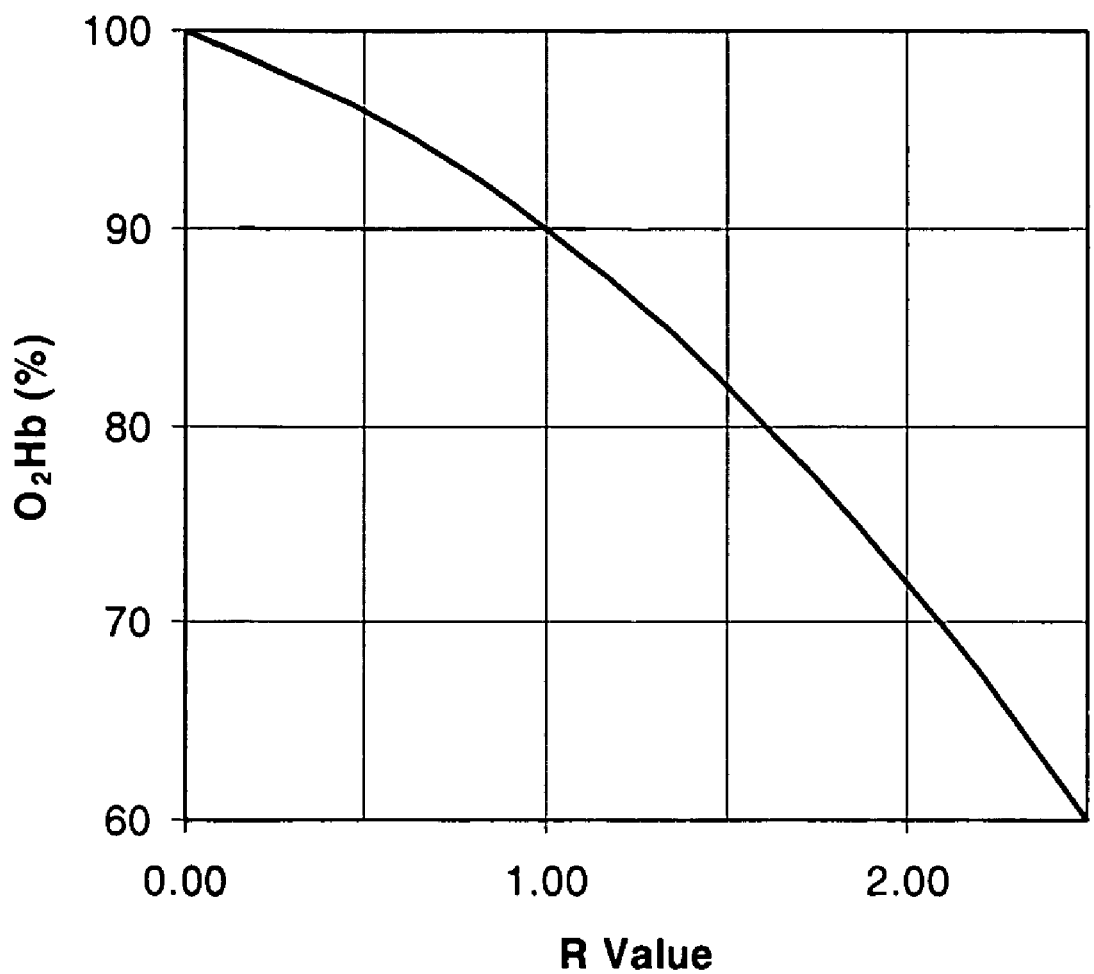
FIG. 1. Calibration, or calibration curve, for a pulse oximeter designed for use on humans.

Plotting $O_2Hb$ data as a function of the associated R values generates a calibration for these data. An example of such a calibration curve, for human use, is shown in FIG. 1. The equation for this curve is a calibration which provides the calculated $O_2Hb$ for any given measured R value. Typically, for a two channel photoplethysmographic device such as a pulse oximeter the calibration equation will take the form:

$$O_2Hb = A \cdot R^2 + B \cdot R + C \quad \text{Equation 2}$$

Where A, B, and C in Equation 2 are calibration constants derived by fitting the calibration curve to a second order polynomial. In pulse oximetry $O_2Hb$ is often termed $S_pO_2$ to designate that it is the arterial oxygen saturation as measured by a pulse oximeter.

Figure 2:
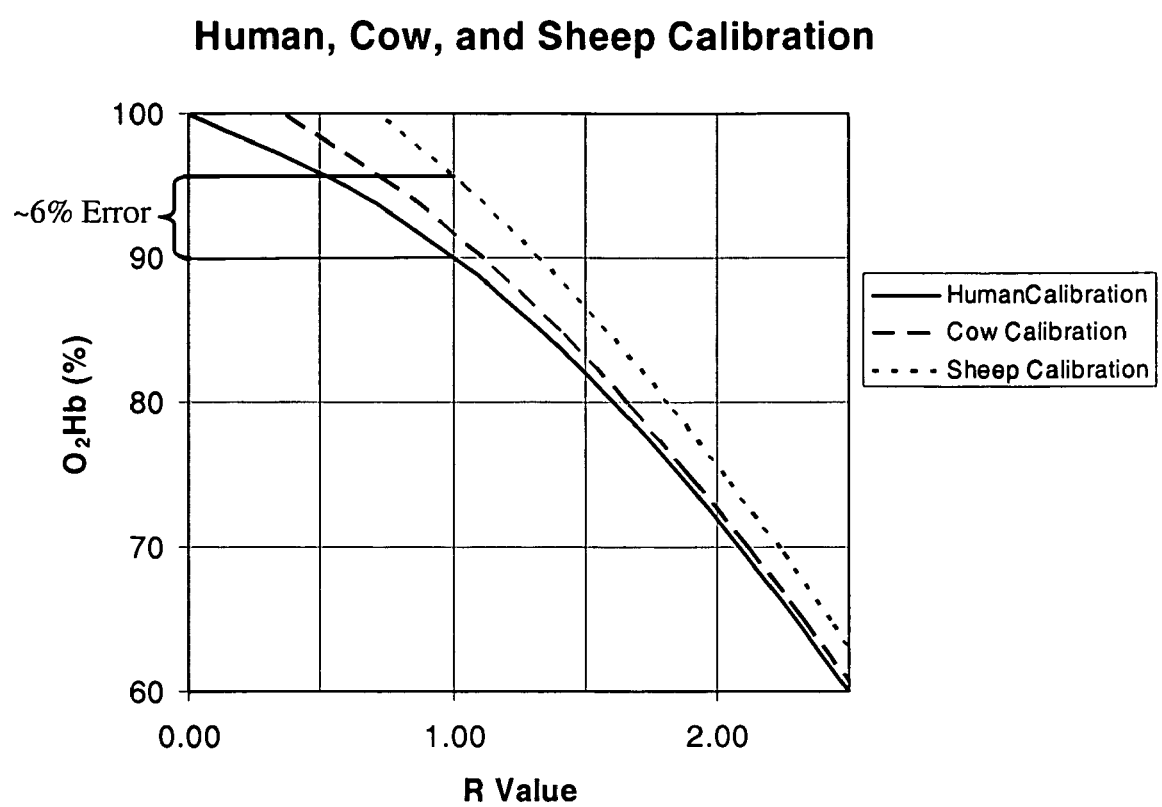
FIG. 2. The calculated errors anticipated by using a human calibration on various different species.

By performing desaturation studies on non-human species it is possible to generate a series of calibration curves such as the ones shown in FIG. 2 for humans, sheep, and cows. These studies are performed on a number of different test subjects over a range of oxygen saturation values and the resultant data is curve fit to give the most accurate calibration for the target species. The calibration curves may alternatively be generated mathematically by using the extinction curves for the hemoglobin of each target species. In this methodology the R value for any given $O_2Hb$ level would be calculated as follows:

$$R = \frac{E_{660}^{O2Hb} \cdot C^{O2Hb} \cdot L + E_{660}^{RHb} \cdot C^{RHb} \cdot L}{E_{900}^{O2Hb} \cdot C^{O2Hb} \cdot L + E_{900}^{RHb} \cdot C^{RHb} \cdot L} \quad \text{Equation 3}$$

In Equation 3: E is the extinction of the superscripted blood analyte ($O_2Hb$ or RHb) at the subscripted wavelength (660 nm or 900 nm); C is the concentration of the superscripted blood analyte; and L is the pathlength of the pulsatile absorbers in the system. Because this pathlength is the same for each term, Equation 3 can be reduced as shown in Equation 4.

$$R = \frac{E_{660}^{O2Hb} \cdot C^{O2Hb} + E_{660}^{RHb} \cdot C^{RHb}}{E_{900}^{O2Hb} \cdot C^{O2Hb} + E_{900}^{RHb} \cdot C^{RHb}} \quad \text{Equation 4}$$

Note that Equation 4 assumes a two component system with only two significant absorbers, $O_2Hb$ and RHb. These equations can be expanded to include additional absorbers as this would simply add more terms, one for each absorber, into the numerator and denominator of this equation. Using the extinction data supplied in the aforementioned reference by W G Zijlstra et al one can then mathematically derive a set of calibrations, or calibration curves, such as those shown in FIG. 2.

Either of these two methods for deriving calibration curves can be used; however, because the mathematical model described above is not an exact match to the actual tissue optics of the physical system, the empirical desaturation methodology always provides a more accurate calibration.

The error that would be obtained by using a pulse oximeter calibrated for humans on a different species can then be calculated by measuring the vertical distance between the human calibration curve and the curve for a different species. An example of this error is shown in FIG. 2 where, for an R value of 1, the human calibration would provide an oxygen saturation of 90% when the true saturation for a sheep at this R value is actually closer to 96%. In this specific case, the error from not calibrating on the correct species would be nearly 6%.

Figure 3:
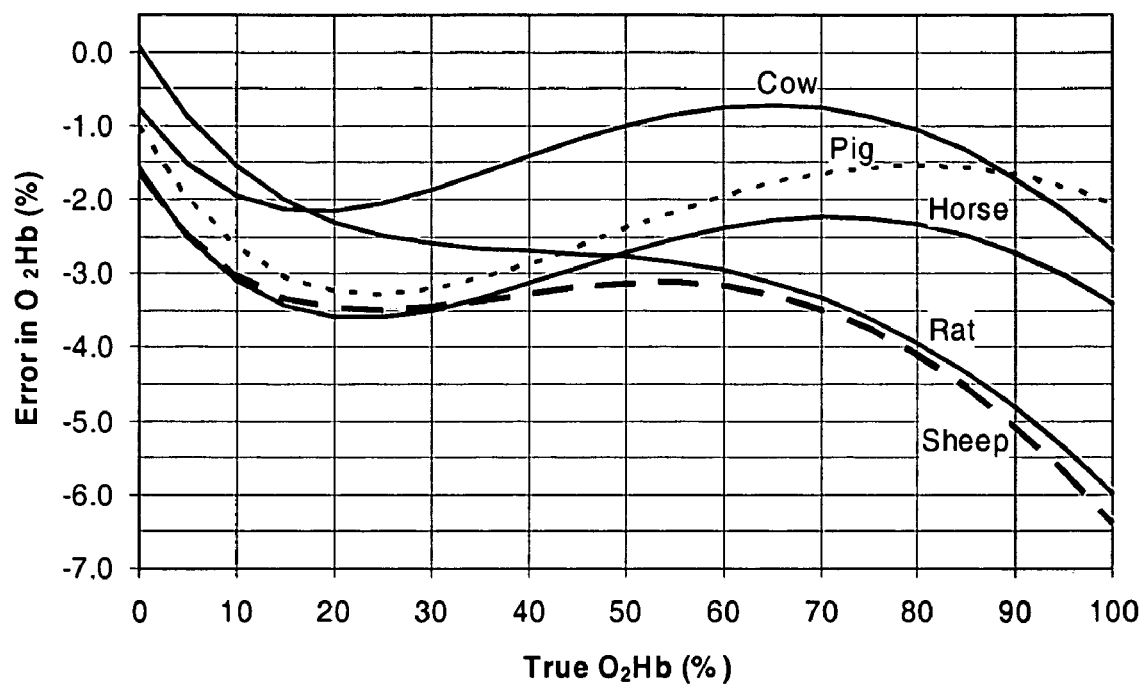
FIG. 3. Calibration curves for various different species generated by applying the errors from FIG. 2 to the empirical calibration curve of FIG. 1.

Expanding this procedure across the entire saturation range, and for a number of different species, generates the data shown in FIG. 3. This graph shows the errors expected, as a function of the true $O_2Hb$, for five different species when a pulse oximeter which is calibrated for use on humans is used on these species.

Installing one or more calibration curves, each derived for a specific non-human species such as the two curves shown in FIG. 2 for cows and sheep, into a photoplethysmographic instrument such as the pulse oximeter and providing a way for the correct calibration curve to be selected for the species being monitored creates an instrument that is accurate across all species for which it is calibrated. The calibration table shown in Table 1 is derived using a second order calibration equation to fit the non-human curves shown in FIG. 2. A, B, and C in this table are the calibration constants for the equation of the form shown in Equation 2. It is these calibration constants that are coded into the instrument software in the current embodiment of this invention.

TABLE 1

| Species | A | B | C |
|---|---|---|---|
| Cow | −3.686 | −7.5825 | 103.02 |
| Sheep | −3.703 | −8.3834 | 107.67 |

Figure 4:
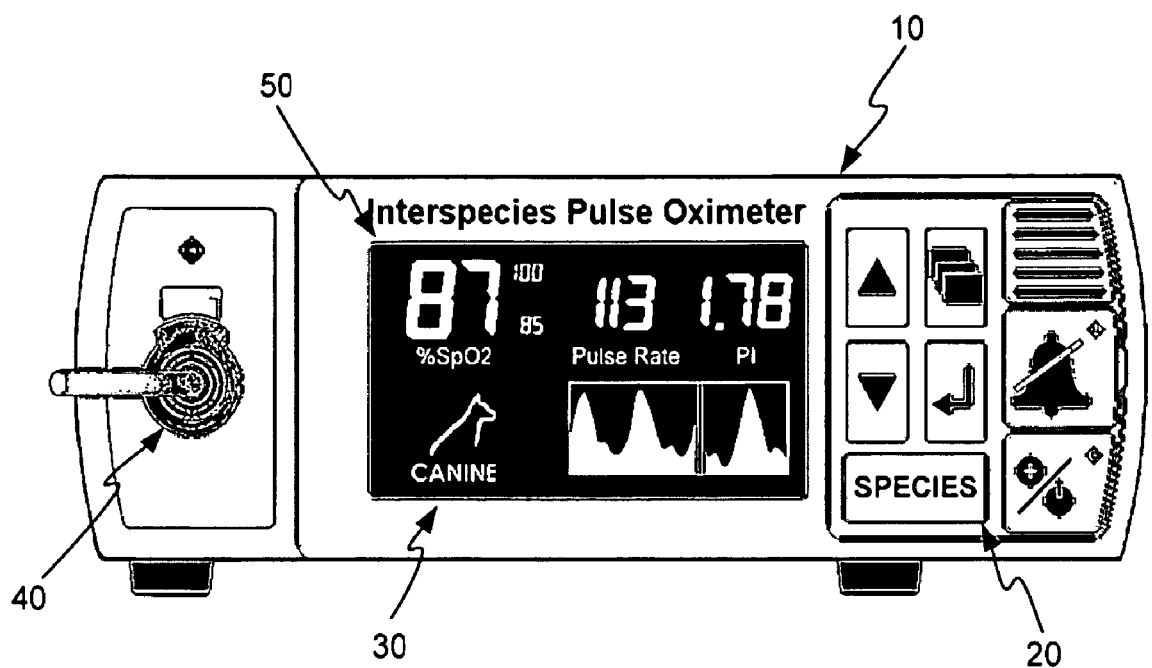
FIG. 4. A schematic representation of an instrument front panel for this invention.

A photoplethysmographic instrument with calibrations for more than one non-human species must provide a means for selection of the desired calibration for the species to be monitored. In the current embodiment of this invention the method for selection of the correct installed calibration is illustrated in FIG. 4. In this figure a schematic representation of the front panel 10 of a pulse oximeter designed for use on multiple non-human species is shown.

The button 20 labeled "SPECIES" is pressed to select the active calibration form the set of calibrations installed in the system software. In the current embodiment of this invention pressing the SPECIES button cycles the active calibration through each of the available species. The species associated with the active calibration is displayed in the "selected species area" 30 of the front panel display 50. In this embodiment it is the responsibility of the operator, i.e. the "user", to select the correct calibration, using the SPECIES button on the instrument, to match the species being monitored.

In an alternate embodiment the active calibration would be provided by, or selected by, the specific sensor that is connected 40 into the instrument. The sensor would contain an identification element, such as a resistor of a set value for a given species, which would be read by the instrument to determine which calibration to use as the active calibration. The identification element could alternatively be a memory device in the form of an integrated circuit which contained the actual calibration. This calibration would then be read by the instrument and used as the active calibration. In this implementation the sensors would be specifically designed to be unique for a given species.

The previous discussion of the invention has been presented for the purposes of illustration and description. The description is not intended to limit the invention to the form disclosed herein. Variations and modifications commensurate with the above are considered to be within the scope of the present invention. The embodiment described herein is further intended to explain the best mode presently known of practicing the invention and to enable others skilled in the art to utilize the invention as such, or in other embodiments, and with the particular modifications required by their particular application or uses of the invention. It is intended that the appended claims be construed to include alternative embodiments to the extent permitted by the prior art.

The invention claimed is:

1. A photoplethysmographic measurement apparatus for measuring one or more blood analyte levels or one or more hemodynamic parameters in a tissue-under-test, comprising:
   one or more emitters generating light incident on a tissue-under-test;
   a detector that receives photoplethysmographic signals from a tissue-under-test and converts the received photoplethysmographic signals to electronic signals indicative of the received photoplethysmographic signals;
   two or more calibrations, each of the calibrations designed for use on a different non-human species;
   a user interface for selection of an active calibration chosen from the two or more calibrations;
   signal processing circuitry which converts the electronic signals into the one or more blood analyte levels or the one or more hemodynamic parameters in accordance with the active calibration.

2. A photoplethysmographic measurement apparatus for measuring one or more blood analyte levels or one or more hemodynamic parameters in a tissue-under-test, comprising:
   one or more emitters generating light incident on a tissue-under-test;
   a detector that receives photoplethysmographic signals from a tissue-under-test and converts the received photoplethysmographic signals to electronic signals indicative of the received photoplethysmographic signals;
   signal processing circuitry which converts the electronic signals into the one or more blood analyte levels or the one or more hemodynamic parameters in accordance with an active calibration selected from two or more calibrations designed for use on two or more non-human species;
   a user interface which provides an interface for selection of the active calibration.

3. A method for photoplethysmographic measurement for measuring one or more blood analyte levels or one or more hemodynamic parameters in a tissue-under-test, comprising the steps of:
   providing two or more calibrations, each of the calibrations designed for a different non-human species;
   directing light into a tissue-under-test;
   detecting photoplethysmographic signals exiting from a tissue-under-test and convening the detected photoplethysmographic signals to electronic signals indicative of the detected photoplethysmographic signals;
   converting the electronic signals into the one or more blood analyte levels or the one or more hemodynamic parameters in accordance with an active calibration;
   selecting the active calibration through the use of a user interface from the two or more calibrations.

4. A method for photoplethysmographic measurement for measuring one or more blood analyte levels or one or more hemodynamic parameters in a tissue-under-test, comprising the steps of:
   directing light into a tissue-under-test;
   detecting photoplethysmographic signals from a tissue-under-test and converting the detected photoplethysmographic signals to electronic signals indicative of the detected photoplethysmographic signals;
   selecting an active calibration through the use of a user interface;
   converting the electronic signals into the one or more blood analyte levels or the one or more hemodynamic parameters in accordance with the active calibration designed for one or more non-human species.

* * * * *